United States Patent
Kim et al.

(10) Patent No.: US 11,215,620 B2
(45) Date of Patent: Jan. 4, 2022

(54) MASS SPECTROMETRY BASED BIOINFORMATICS PLATFORM FOR HIGH-THROUGHPUT IDENTIFICATION OF GLYCATION PROTEINS AND ADVANCED GLYCATION END-PRODUCTS

(71) Applicant: Korea Basic Science Institute, Daejeon (KR)

(72) Inventors: Jin Young Kim, Cheongju-si (KR); Gun Wook Park, Cheongju-si (KR); Eun Sun Ji, Daejeon (KR); Jong Shin Yoo, Seoul (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 0 days.

(21) Appl. No.: 16/296,154

(22) Filed: Mar. 7, 2019

(65) Prior Publication Data

US 2019/0285645 A1  Sep. 19, 2019

(30) Foreign Application Priority Data

Mar. 13, 2018  (KR) .......................... 10-2018-0029350

(51) Int. Cl.
*G01N 33/68* (2006.01)
*G16B 15/00* (2019.01)
*G06F 17/16* (2006.01)

(52) U.S. Cl.
CPC ......... *G01N 33/6848* (2013.01); *G06F 17/16* (2013.01); *G16B 15/00* (2019.02)

(58) Field of Classification Search
None
See application file for complete search history.

(56) References Cited

FOREIGN PATENT DOCUMENTS

| KR | 10-2011-0042607 | | 5/2011 |
|---|---|---|---|
| KR | 10-2012-0108011 | | 9/2012 |
| KR | 10-1202585 | B1 | 11/2012 |
| KR | 10-1243183 | B1 | 3/2013 |
| KR | 10-2015-0015718 | A | 2/2015 |
| KR | 10-2018-0068238 | A | 6/2018 |

(Continued)

OTHER PUBLICATIONS

Park, G.W. et al. Integrated GlycoProteome Analyzer (I-GPA) for Automated Identification and Quantitation of Site-Specific N-Glycosylation, Scientific Reports, vol. 6, pp. 21175-1-21175-12 (Year: 2016).*

(Continued)

*Primary Examiner* — Xiaoyun R Xu
(74) *Attorney, Agent, or Firm* — Workman Nydegger

(57) ABSTRACT

The preset invention relates to a high resolution mass spectrometry based novel bioinformatics platform for the identification of glycation proteins and advanced glycation end-product. Particularly, the bioinformatics platform of the present invention facilitates an efficient and accurate investigation of quantitative changes of glycation proteins and advanced glycation end-products which are included in various types of samples but had not been informed yet, and uses a high resolution mass spectrometry, and thereby can be effectively used for the prediction or diagnosis of a disease including cancer by examining a disease marker in a sample.

17 Claims, 11 Drawing Sheets

Specification includes a Sequence Listing.

(56) References Cited

FOREIGN PATENT DOCUMENTS

WO    2014147395    9/2014

OTHER PUBLICATIONS

Filev, P. et al. Comparison of similarity measures for the task of template matching of masses on serial mammograms, Medical Physics, vol. 32(2), pp. 515-529 (Year: 2005).*
Rabbani, N. et al. Glycation research in amino acids: a place to call home, Amino acids, 2012, 42, 1087-1096 (Year: 2012).*
Lynn et al. "MAGIC: An Automated N-Linked Glycoprotein Identification Tool Using a Y1-Ion Pattern Matching Algorithm and in Silico MS2 Approach" Analytical Chemistry, 2015, 87, 4, pp. 2466-2473.

* cited by examiner

Results of proteome Discoverer Search

| High | [K].SJHTLFGDKLCTVATLR.[E] | 1xCarbamidomethyl [C11] | PA12768 1xHex [K97] | 0.00902254 | 0 | 1 | K.SJHTLFGDKLCTVATLR.E | |
|---|---|---|---|---|---|---|---|---|
| Checked | Confidence | Identifying Node | PSM Ambiguity | Annotated Sequence | Modifications | Charge | MH+ [Da] | First Scan |
| FALSE | high | Sequest HT (A2) | Unambiguous | [K].SJHTLFGDKLCTVATLR.[E] | K9(Hex);C11(Carbamidomethyl) | 2 | 2094.09184 | 20628 |
| FALSE | high | Sequest HT (A2) | Unambiguous | [K].SJHTLFGDKLCTVATLR.[E] | K9(Hex);C11(Carbamidomethyl) | 3 | 2094.09079 | 20624 |
| FALSE | high | Sequest HT (A2) | Unambiguous | [K].SJHTLFGDKLCTVATLR.[E] | K9(Hex);C11(Carbamidomethyl) | 3 | 2094.09061 | 20742 |
| FALSE | high | Sequest HT (A2) | Unambiguous | [K].SJHTLFGDKLCTVATLR.[E] | K9(Hex);C11(Carbamidomethyl) | 4 | 2094.09096 | 20623 |
| FALSE | high | Sequest HT (A2) | Unambiguous | [K].SJHTLFGDKLCTVATLR.[E] | K9(Hex);C11(Carbamidomethyl) | 4 | 2094.0917 | 20741 |

Identified Peptide Group

FIG. 5

MASS SPECTROMETRY BASED BIOINFORMATICS PLATFORM FOR HIGH-THROUGHPUT IDENTIFICATION OF GLYCATION PROTEINS AND ADVANCED GLYCATION END-PRODUCTS

CROSS-REFERENCE TO RELATED APPLICATIONS

This application claims priority to Korean Patent Application No. 10-2018-0029350, filed on Mar. 13, 2018, the entirety of which is incorporated herein by reference.

BACKGROUND OF THE INVENTION

1. The Field of the Invention

The preset invention relates to a high resolution mass spectrometry based novel bioinformatics platform for the identification of glycation proteins and advanced glycation end-products.

2. Description of the Related Art

Human blood is a mixture of many proteins. Among those proteins, the proteins being used as a substrate for glycation takes 70% of the human body composition. However, glycation proteins and advanced glycation end-products (AGE) are difficult to analyze qualitatively or quantitatively as compared to proteome analysis due to the diversity and complexity of sugar. Recently, the analysis of glycation proteins and advanced glycation end-products has been rapidly developed by the introduction of high resolution mass spectrometry. However, bioinformatics technique to identify and quantify glycation proteins and advanced glycation end-products using the results obtained by the mass spectrometry above is still in need.

The glycation is a reaction wherein the amino group ($NH^{3+}$) of a protein binds to the carbonyl group (C=O) of a reducing sugar. During the glycation reaction, fructose or glucose molecules bind to lysine or arginine. Thereafter, oxidation or an additional reaction with other peptides or proteins follows, resulting in the production of irreversible glycation products or glycation protein masses, which are called advanced glycation end-products. At this time, the resultant glycation products or glycation protein masses lose their original functions as proteins.

That is, glycation is a process in which a protein is combined with a sugar floating in blood to form an advanced glycation end-product. The advanced glycation end-product is a chemically unstable and highly reactive material, so that it attacks tissues and cells in vivo.

As soon as the end-product is created, the gene is activated and a receptor, an end-product receptor, is created that can bind end-products to cell membranes such as blood vessel walls or lymphocytes. Once an advanced glycation end-product is produced, a specific gene is activated to produce an advanced glycation end-product receptor (RAGE: Receptor of AGE) that can bind to the advanced glycation end-product on the blood vessel wall or the membrane of cells such as lymphocytes. When an advanced glycation end-product is bound to the corresponding advanced glycation end-product receptor, various immune factors related to inflammation are activated and the activated immune factors cause various diseases or aging. At last, the advanced glycation end-product becomes a major causing substance of various diseases and aging of the body due to its effect on cells and biomolecules.

Since the human body function is caused by proteins, damage of intrinsic functions of proteins can directly lead to a disease. The advanced glycation end-products are known to be associated with adult diseases such as aging, Alzheimer's disease, kidney disease, diabetes, diabetic vascular complications, diabetic retinopathy, and diabetic neuropathy by increasing vascular permeability, inhibiting vasodilatation by suppressing nitric oxide, oxidating LDL (low-density lipoprotein), increasing the secretion of various cytokines in macrophages or endothelial cells, and increasing oxidative stress.

Therefore, if qualitative and quantitative analysis of the advanced glycation end-product included in blood is accomplished, biomarkers for various diseases would be identified. In relation to the above, Korean Patent No. 10-1243183 describes a fluorescence measurement device that can evaluate various diseases relating to diabetes by measuring self-fluorescence of the advanced glycation end-product accumulated in the skin.

CIVIL (carboxymethyl lysine) and CEL (carboxyethyl lysine), the modified glycation structures to the lysine site of the predicted protein including albumin bound to the advanced glycation end-product receptor in blood, and MG-H1 (methylglyoxal-derived hydroimidazolene), the modified glycation structures to the arginine site, have been mostly studied. GOLD (glyoxal lysine dimer) and MOLD (methylglyoxal-lysine dimer) are also known in the form of dimers. In addition, since the modified glycation structure is formed in a variety of structures, it is limited to confirm these various types of advanced glycation end-products. Therefore, it is requested to develop a novel method for qualitative and quantitative analysis of glycation proteins and advanced glycation end-products.

To overcome the limitation above, the present inventors studied and identified the initial glycation structure FL (fructosyl-lysine) and the representative lysine glycation structure CIVIL and the representative arginine glycation structure MG-H1, among many advanced glycation end-products, by using not the database for total structure but the software to search for existing proteins (Proteome Discoverer, Thermo Fisher Scientific), and further developed a software to screen an additional glycation structure based on the newly established standard database, leading to the completion of the present invention.

BRIEF SUMMARY OF THE INVENTION

It is an object of the present invention to provide a novel method for identifying glycation proteins and advanced glycation end-products with a low sensitivity (or concentration), compared with non-glycation peptides.

To achieve the object above, the present invention provides a method for identifying glycation proteins and advanced glycation end-products comprising the following steps: 1) obtaining mass spectrum by analyzing the polypeptide obtained from hydrolysis of the protein included in the sample with high-resolution mass spectrometry; 2) converting the mass spectrum results obtained in step 1) into MS (mass spectrometry) and tandem spectrum (MS/MS); 3) identifying proteins from the tandem spectrum results transformed in step 2); 4) grouping the proteins identified in step 3) above according to the peptide sequence into a) and b) below, precisely a) non-glycation peptides and b) glycation peptides and advanced glycation end-products; 5) generating a regular pattern by normalizing the intensities of b-ions and y-ions excluding the glycation sites in each group spectrum obtained from a) and b) grouped in step 4) above; and 6) selecting novel glycation peptides and advanced glycation end-product peptides showing a similar pattern to the regular pattern generated in step 5) above.

Advantageous Effect

The bioinformatics platform of the present invention facilitates an efficient and accurate investigation of quantitative changes of glycation proteins and advanced glycation end-products which are included in various types of samples but had not been informed yet, and uses a high resolution mass spectrometry, and thereby can be effectively used for the prediction or diagnosis of a disease including cancer by examining a disease marker in a sample.

BRIEF DESCRIPTION OF THE DRAWINGS

FIG. 5 is a diagram illustrating the grouping process of the glycation peptides selected from the commercial glycated human serum albumin.

DETAILED DESCRIPTION OF THE PREFERRED EMBODIMENTS

Figure 1:
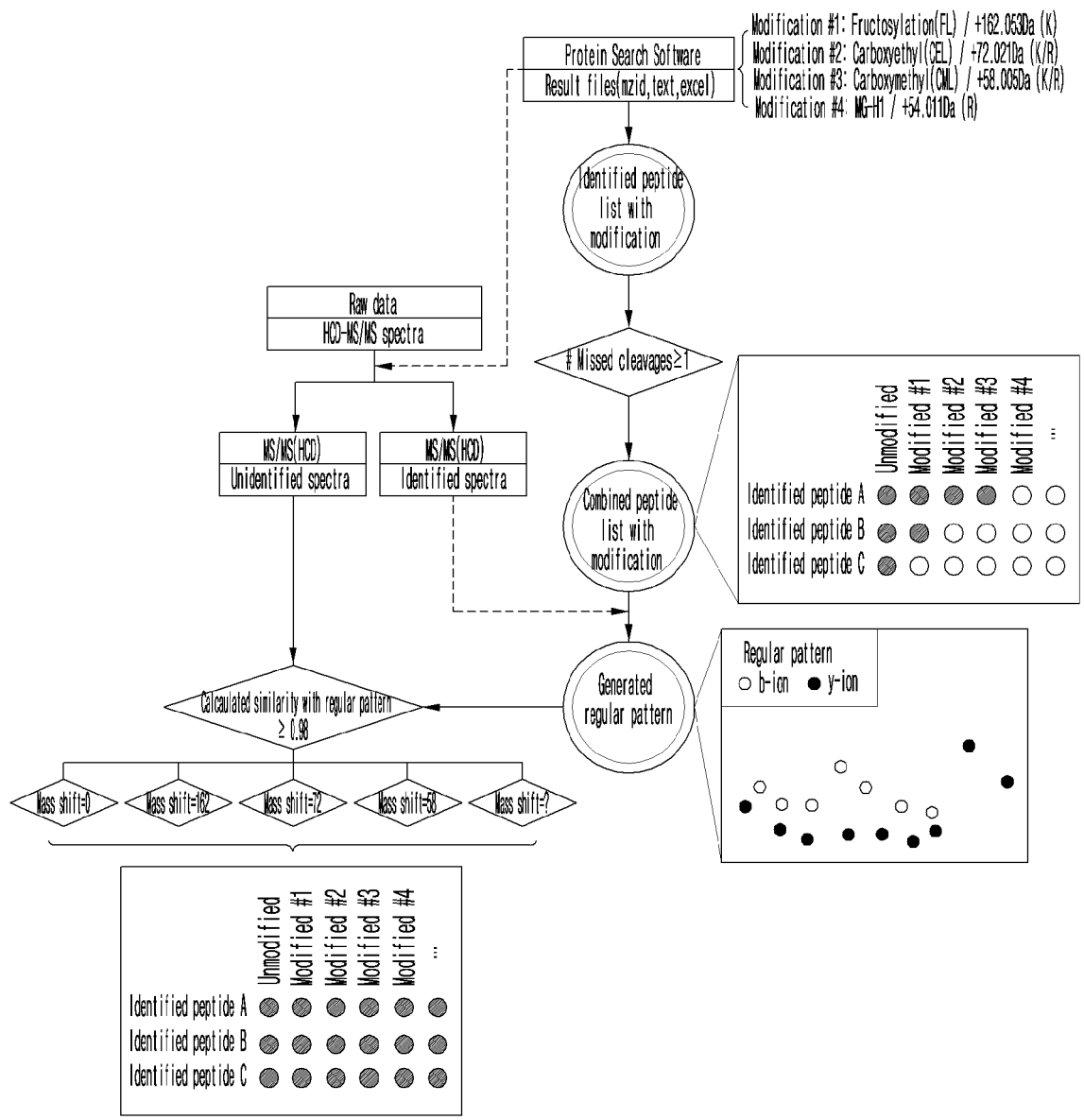
FIG. 1 is a flowchart illustrating the method for identifying glycation proteins and advanced glycation end-products according to the present invention.

Hereinafter, the present invention is described in detail.

The present invention provides a method for identifying glycation proteins and advanced glycation end-products comprising the following steps: 1) obtaining mass spectrum by analyzing the polypeptide obtained from hydrolysis of the protein included in the sample with high-resolution mass spectrometry; 2) converting the mass spectrum results obtained in step 1) into MS (mass spectrometry) and tandem spectrum (MS/MS); 3) identifying proteins from the tandem spectrum results transformed in step 2); 4) grouping the proteins identified in step 3) above according to the peptide sequence into a) and b) below, precisely a) non-glycation peptides and b) glycation peptides and advanced glycation end-products; 5) generating a regular pattern by normalizing the intensities of b-ions and y-ions excluding the glycation sites in each group spectrum obtained from a) and b) grouped in step 4) above; and 6) selecting novel glycation peptides and advanced glycation end-product peptides showing a similar pattern to the regular pattern generated in step 5) above.

The hydrolysis above can be performed using any methods well known to those in the art. Particularly, the hydrolysis can be performed with one or more enzymes selected from the group consisting of trypsin, arginine C (Arg-C), aspartic acid N (Asp-N), glutamic acid C (Glu-C), lysine C (Lys-C), chymotrypsin and proteinase K.

The platform of the present invention can use a mass spectrometer to efficiently quantitatively and qualitatively analyze the glycation proteins and the advanced glycation end-products, which have more complicated structure than the non-glycated peptides, have a high diversity and exist at a low concentration in a sample. The mass spectrometer can have a mass resolution of 10,000 or more and a mass accuracy of 50 ppm or less. Particularly, the mass spectrometer can be Orbitrap Fusion Lumos, Orbitrap Elite, or Q Exactive.

The term "tandem spectrum (MS/MS)" used in this invention refers to the spectrum obtained by analyzing the ions in interest or the ions with relatively high sensitivity among the total mass spectrum (MS). By analyzing the mass of the tandem spectrum, tandem mass spectrometry can be performed, and the resultant tandem spectrum can be used to select known glycation proteins and advanced glycation end-products. The tandem spectrum can be CID (collision-induced dissociation) or HCD-MS/MS (high energy collision dissociation-MS/MS) spectrum.

The identification of the protein in the method according to the present invention can be performed using any software known as software for screening glycation proteins and advanced glycation end-products using the tandem spectrum results. For example, such software as Proteome Discoverer 1.1.0.263 software (Thermo Fisher Scientific), Mascot (Matrix Science, http://www.matrixscience.com/) or IP2 (Integrated Proteomics Pipeline, http://www.integratedproteomies.com/) can be used.

The protein identified by the informatics platform of the present invention can be grouped according to the peptide sequence as follows:

a) non-glycated peptides; and
b) glycation peptides and advanced glycation end-product peptides.

In the grouping process above, the glycation peptides and the advanced glycation end-product peptides can also be grouped if they have the glycation form known to those in the art. Particularly, the peptides can have one or more glycation transformation forms selected from the group consisting of fructosylation, carboxyethyl, carboxymethyl and MG-H11 (methylglyoxal-derived hydroimidazolene).

In the method according to the present invention, the step of generating a regular pattern can include the process of comparing the tandem spectrum of each of the non-glycated peptides in which K or R amino acid residue has not been glycated in b-ions or y-ions which are the theoretically fragmented ions in the spectra of a) non-glycated peptides and b) glycation peptides and advanced glycation end-product peptides can be included. In addition, a regular pattern can be generated by extracting the mass value and the intensity of the fragmented ions from the comparison results, and finally obtaining the average of the mass value and the intensity of all the tandem spectra. The generated regular pattern can be used to construct a database.

In the method according to the present invention, the regular pattern generated by using the spectra of the non-glycated peptide group and the glycation peptide/advanced glycation end-product peptide group can be used for the selection of novel glycation peptides and advanced glycation end-product peptides. At this time, in order to select the peptides showing similar pattern to the regular pattern, the Regular Pattern Similarity (RPS) calculated by the following mathematical formula 1 can be used:

$$RPS = \frac{\sum_{i=1}^{n} S_i \times S'_i}{\sqrt{\sum_{i=1}^{n} S_i^2 \times \sum_{i=1}^{n} S'^2_i}}$$ [Mathematical Formula 1]

(S: mass (x) and relative peak intensity (y) of tandem mass spectrometry spectrum,
Si: (x, y) matrix, wherein x is the $n^{th}$ relative peak intensity, and y is the $n^{th}$ peak mass, and
S'i: (x', y') matrix, wherein x' is the $n^{th}$ relative peak intensity, and y' is the $n^{th}$ peak mass)

The platform of the present invention can additionally include one or more steps selected from the group consisting of evaluating the selected glycation peptides and advanced glycation end-product peptides using the molecular weight difference (shift); and analyzing the selected glycation peptides and advanced glycation end-product peptides quantitatively.

The evaluation above can be performed by selecting the peptides having tandem spectrum similar to the regular pattern using the spectral similarity calculated by mathematical formula 1 according to the present invention and calculating the molecular weight difference of the mass value (MH+) of each tandem spectrum of those selected peptides and the peptides having the regular pattern. Using the calculated molecular weight difference, it can be confirmed that the selected peptides have one or more glycation transformation forms selected from the group consisting of fructosylation, carboxyethyl, carboxymethyl and MG-H11.

In the meantime, in the step of analyzing quantitatively above, the quantitative analysis can be achieved by combining the intensities of the three theoretically strongest peaks among the isotope peaks presenting the intensities of the glycation peptides and advanced glycation end-product peptides selected from MS spectra.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Analysis of Glycated Human Serum Albumin (HSA) Product Data

The commercial human serum albumin was purchased from Sigma-Aldrich. Trypsin was added to the purchased glycated human serum albumin, followed by hydrolysis at 37° C. for overnight. As a result, the hydrolyzed sample was obtained. The polypeptides contained in the sample were analyzed by liquid chromatography-tandem mass spectrometry using the hydrolyzed sample. The analysis was performed as shown in FIG. 1. Particularly, peptide groups were identified by analyzing four types of the glycation transformation forms known in tandem spectrum as parameters using protein search software. Then, new glycation sites and structure of albumin protein were further analyzed by using the regular pattern of each identified peptide group.

Figure 2:
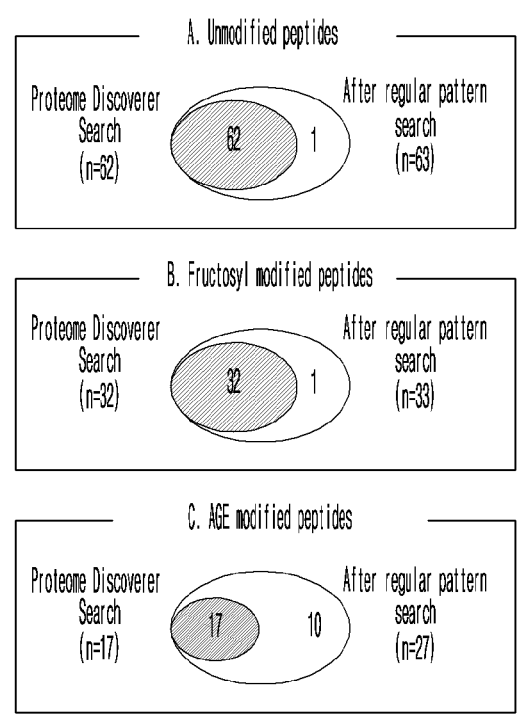
FIG. 2 is a diagram illustrating the results of comparing non-glycation proteins (A), glycation proteins (B) and advanced glycation end-products (C) from the commercial glycated human serum albumin before and after the regular pattern analysis.
Figure 3:
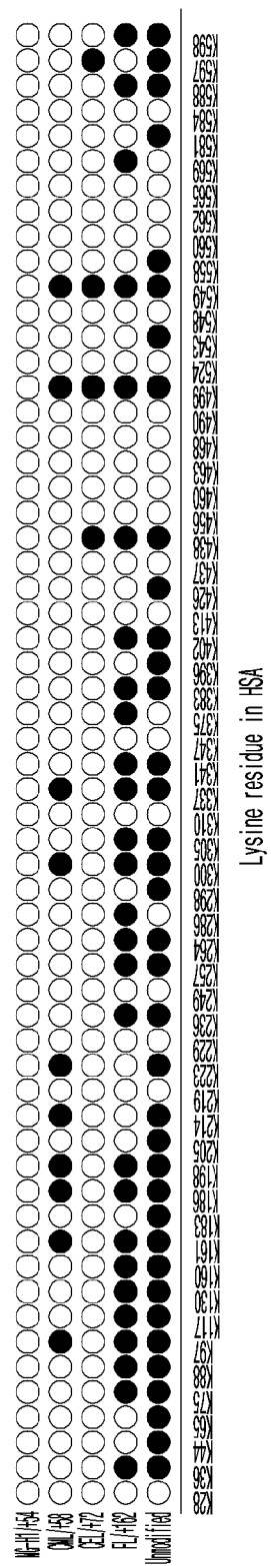
FIG. 3 is a diagram illustrating the glycation sites in the glycation proteins and the advanced glycation end-products selected from the commercial glycated human serum albumin, precisely the locations of lysine.
Figure 4:
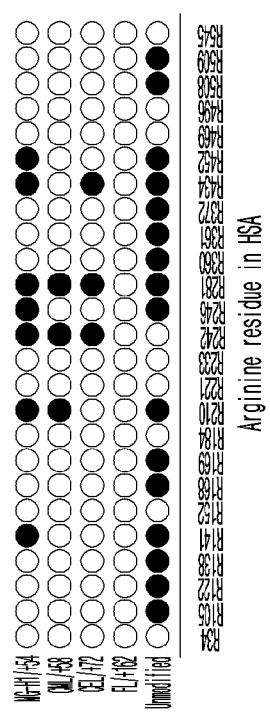
FIG. 4 is a diagram illustrating the glycation sites in the glycation proteins and the advanced glycation end-products selected from the commercial glycated human serum albumin, precisely the locations of arginine.

As a result, as shown in FIG. 2 to FIG. 4, glycation sites for 30 lysines and 7 arginines were confirmed, and finally total 60 glycation peptides were identified.

Figure 6:
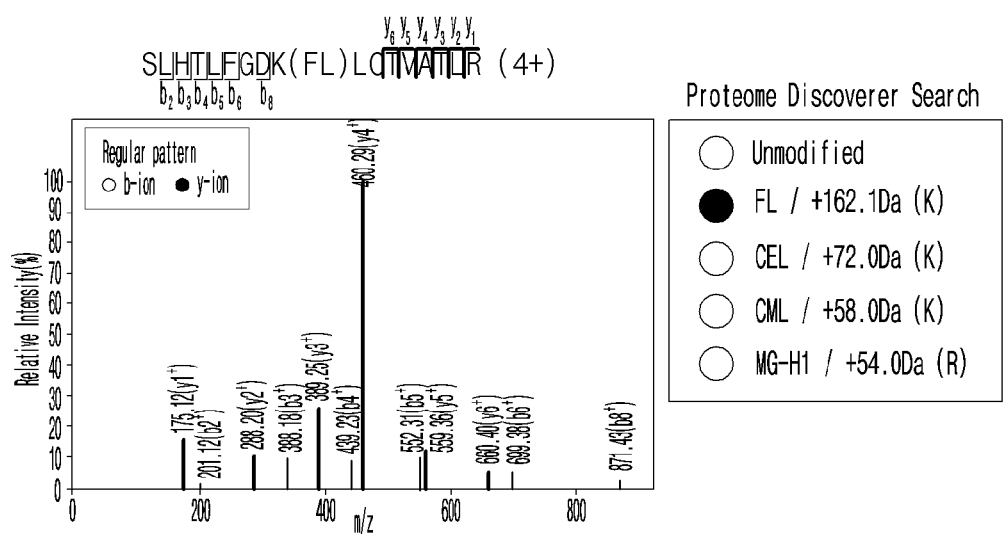
FIG. 6 is a diagram illustrating the generating process of regular pattern.
Figure 7:
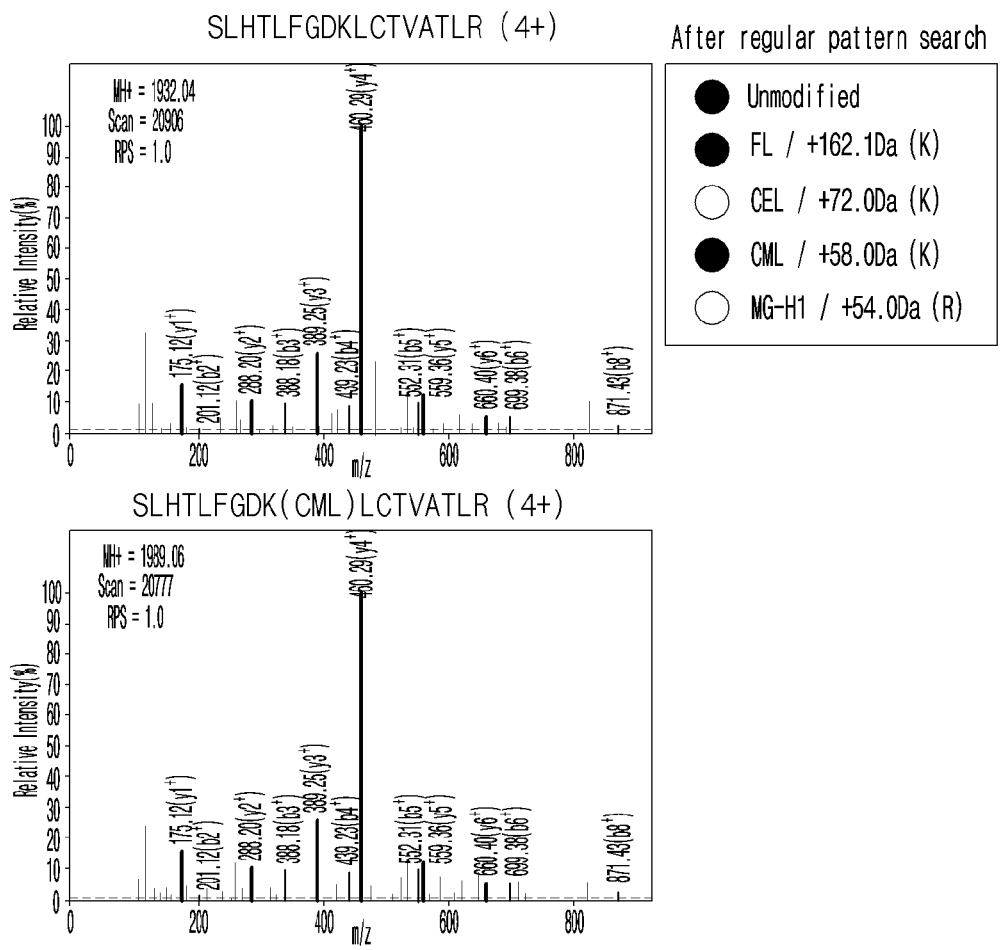
FIG. 7 is a diagram illustrating the selecting process of the novel glycation peptides.

In the meantime, one of those identified glycation peptides was presented in FIG. 5 to FIG. 7 as an example. Particularly, as shown in FIG. 5 to FIG. 7, in the first step, the peptide having the amino acid sequence represented by SEQ. ID. NO: 1, identified above, was grouped into the peptide type of SLHTLFGDK(FL)LCTVATLR(4+) in which the 9th K was glycated to FL (FIG. 5). Next, a regular pattern was generated using the grouped SLHTLFGDK(FL)LCTVATLR(4+) type peptide (FIG. 6). Finally, peptides similar to the generated regular pattern were screened and as a result novel glycation peptides were identified (FIG. 7).

Figure 8:
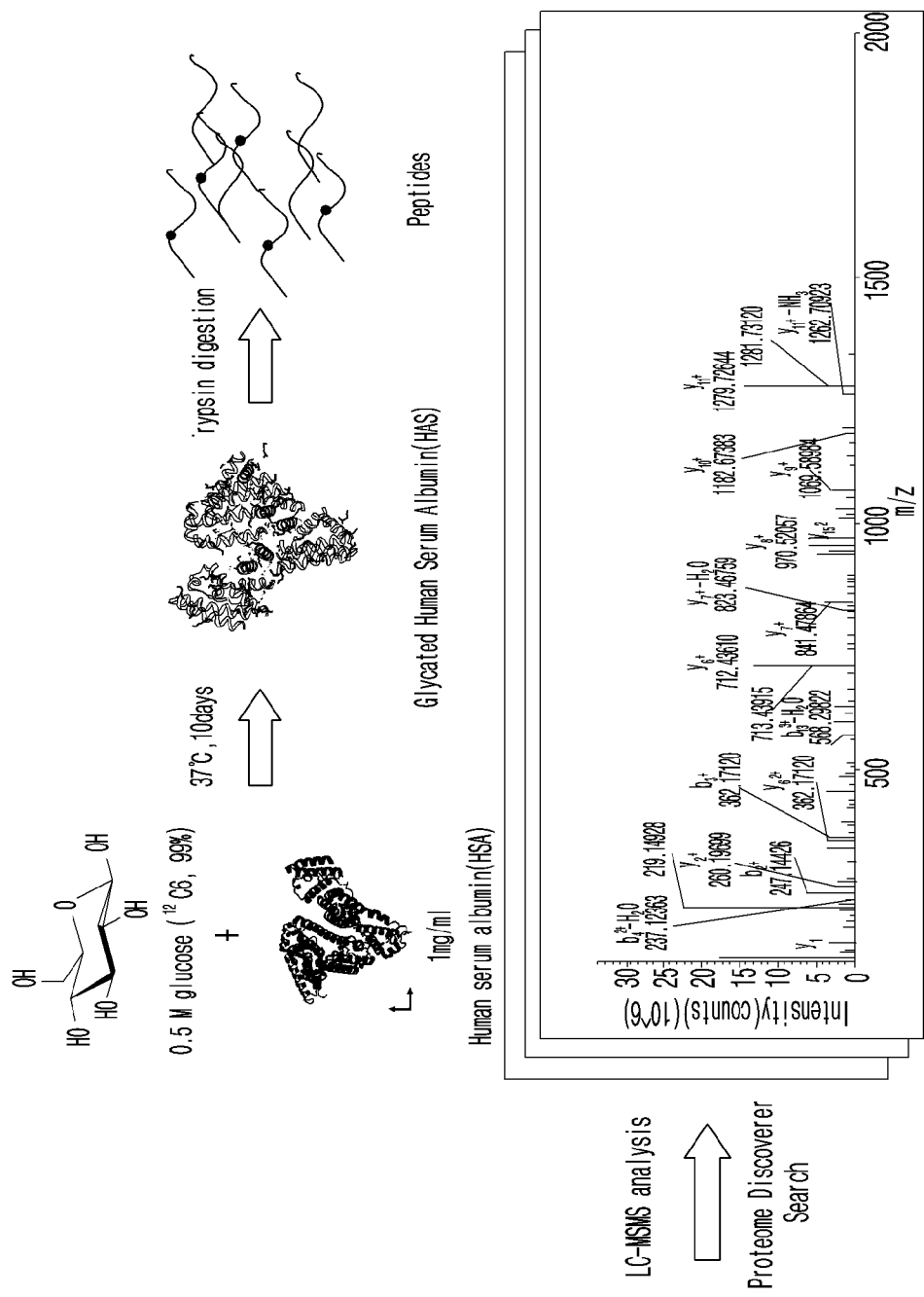
FIG. 8 is a flowchart illustrating the process of glycation of human serum albumin to prepare a glycation sample.

Example 2: Preparation of Glycated Sample of Human Serum Albumin and Data Analysis Glucose (1 mg/me) was added to a human serum albumin sample purchased from Sigma Aldrich at the concentration of 0.5 M, followed by reaction at 37° C. for 7 days, resulting in the preparation of a glycated sample of human serum albumin. Upon completion of the reaction, trypsin was added to the glycated sample, followed by hydrolysis at 37° C. for overnight. LC/ESI-MS/MS analysis was performed by loading the hydrolyzed polypeptide to Orbitrap Fusion Lumos (Orbitrap Fusion™), a high resolution mass spectrometer. Glycation sites of the peptides consisting glycation proteins and advanced glycation end-products were investigated with the novel method of the present invention in order to identify glycation proteins and advanced glycation end-products using the result data of the mass spectrometry above (FIG. 8).

Figure 9:
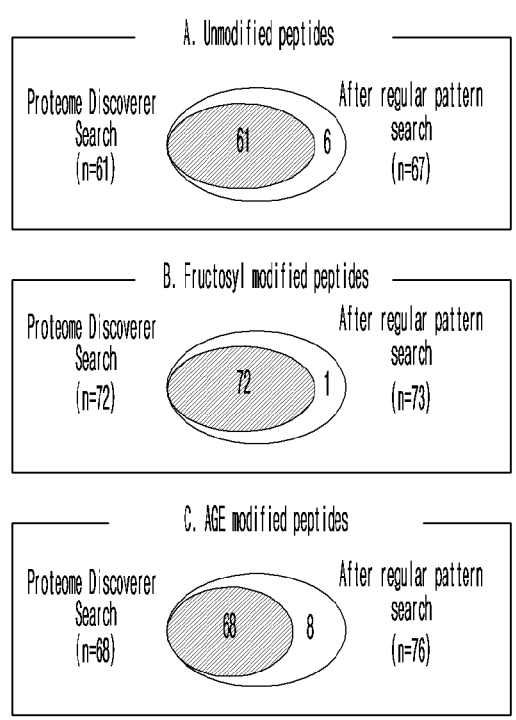
FIG. 9 is a diagram illustrating the results of comparing non-glycation proteins (A), glycation proteins (B) and advanced glycation end-products (C) from the prepared glycated human serum albumin before and after the regular pattern analysis.
Figure 10:
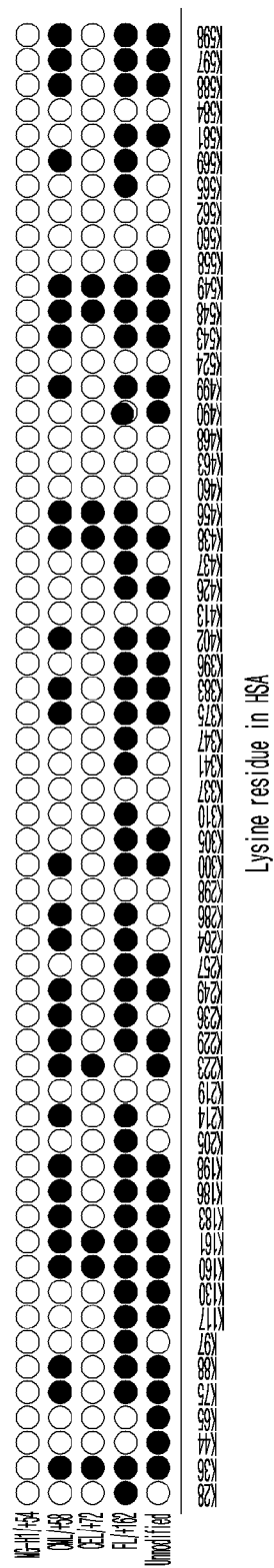
FIG. 10 is a diagram illustrating the glycation sites in the glycation proteins and the advanced glycation end-products (C) selected from the prepared glycated human serum albumin, precisely the locations of lysine.
Figure 11:
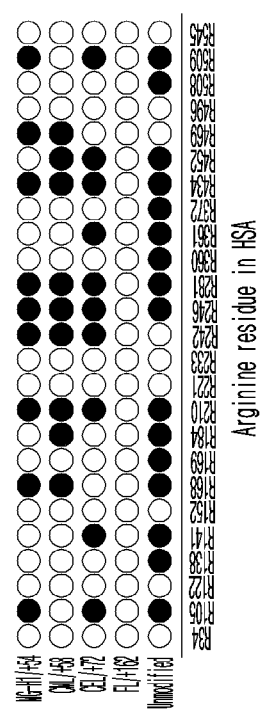
FIG. 11 is a diagram illustrating the glycation sites in the glycation proteins and the advanced glycation end-products (C) selected from the prepared glycated human serum albumin, precisely the locations of arginine.

As a result, as shown in FIG. 9 to FIG. 11, the glycation peptides having the different advanced glycation end-product structures including not only FL but also CIVIL (Carboxymethyl-lysine) and MG-H1 (Methylglyoxal-derived hydroimidazolene) were confirmed.

What is claimed is:

1. A method for identifying glycation proteins and advanced glycation end-products comprising the following steps:
   (1) obtaining mass spectrum by analyzing polypeptides obtained from hydrolysis of protein included in a sample with a high-resolution mass spectrometer, the sample comprising (i) non-glycation peptides and (ii) glycation peptides and advanced glycation end-products having one or more glycation transformation(s) occurring at lysine amino acid residue(s) and/or arginine amino acid residue(s), the glycation transformation(s) selected from the group consisting of fructosylation (FL), carboxyethyl (CEL), carboxymethyl (CIVIL), and methylglyoxal-derived hydroimidazolene (MG-H11);
   (2) converting the mass spectrum obtained in step (1) into:
       mass spectrum (MS); and
       tandem spectrum (MS/MS);
   (3) identifying peptides from the tandem spectrum converted in step (2);
   (4) grouping the peptides identified in step (3) according to peptide sequence into:
       group (a): non-glycation peptides; and
       group (b): glycation peptides and advanced glycation end-products, the glycation peptides and advanced glycation end-products having one or more glycation transformation(s) occurring at lysine amino acid residue(s) and/or arginine amino acid residue(s) other than C-terminal lysine amino acid residue(s) and/or arginine amino acid residue(s), the glycation transformation(s) selected from the group consisting of fructosylation (FL), carboxyethyl (CEL), carboxymethyl (CML), and methylglyoxal-derived hydroimidazolene (MG-H11);
   (5) generating a regular pattern by:
       extracting a mass value and an intensity of glycation free b-ions or glycation free y-ions in tandem spectrum of identified peptide; and
       normalizing intensities of glycation free b-ions and glycation free y-ions; and
   (6) selecting novel glycation peptides and advanced glycation end-product peptides showing a similar tandem spectrum pattern to the regular pattern generated in step (5) but having a molecular weight difference due to having one or more glycation transformations selected from the group consisting of fructosylation (FL), carboxyethyl (CEL), carboxymethyl (CML), and methylglyoxal-derived hydroimidazolene (MG-H11).

2. The method for identifying glycation proteins and advanced glycation end-products according to claim 1, wherein step (6) is performed by calculation with Mathematical Formula 1:

$$RPS = \frac{\sum_{i=1}^{n} S_i \times S_i'}{\sqrt{\sum_{i=1}^{n} S_i^2 \times \sum_{i=1}^{n} S_i'^2}}$$ [Mathematical Formula 1]

wherein:
S: mass (x) and relative peak intensity (y) of tandem mass spectrometry spectrum,
Si: (x, y) is a vector of peptide mass spectrum patterns, wherein x is the $n^{th}$ relative peak intensity, and y is the $n^{th}$ peak mass, and
S'i: (x', y') is a vector of peptide mass spectrum patterns, wherein x' is the $n^{th}$ relative peak intensity, and y' is the $n^{th}$ peak mass.

3. The method for identifying glycation proteins and advanced glycation end-products according to claim 1, wherein the hydrolysis is performed by using one or more enzymes selected from the group consisting of trypsin, arginine C (Arg-C), aspartic acid N (Asp-N), glutamic acid C (Glu-C), lysine C (Lys-C), chymotrypsin and proteinase K.

4. The method for identifying glycation proteins and advanced glycation end-products according to claim 1, wherein the mass spectrometer has a mass resolution of 10,000 or more and a mass accuracy of 50 ppm or less.

5. The method for identifying glycation proteins and advanced glycation end-products according to claim 4, wherein the mass spectrometer is Orbitrap Fusion Lumos, Orbitrap Elite, or Q Exactive.

6. The method for identifying glycation proteins and advanced glycation end-products according to claim 1, wherein step (6) further comprises evaluating the selected glycation peptides and advanced glycation end-product peptides using molecular weight difference (shift).

7. The method for identifying glycation proteins and advanced glycation end-products according to claim 1, wherein step (6) further comprises analyzing the selected glycation peptides and advanced glycation end-product peptides quantitatively.

8. The method for identifying glycation proteins and advanced glycation end-products according to claim 7, wherein the analysis is performed by combining the intensities of the three theoretically strongest peaks among the isotope peaks presenting the intensities of the glycation peptides and advanced glycation end-product peptides selected from MS spectra.

9. A method for identifying glycation proteins and advanced glycation end-products comprising the following steps:

(1) obtaining mass spectrum by analyzing polypeptides obtained from hydrolysis of protein included in a sample with a high-resolution mass spectrometer;

(2) converting the mass spectrum obtained in step (1) into:
mass spectrum (MS); and
tandem spectrum (MS/MS);

(3) identifying peptides from the tandem spectrum converted in step (2);

(4) grouping the peptides identified in step (3) according to peptide sequence into:
group (a): non-glycation peptides; and
group (b): glycation peptides and advanced glycation end-products having one or more glycation transformation(s) occurring at lysine amino acid residue(s) and/or arginine amino acid residue(s) other than C-terminal lysine amino acid residue(s) and/or arginine amino acid residue(s);

(5) generating a regular pattern by:
extracting a mass value and an intensity of glycation free b-ions or glycation free y-ions in tandem spectrum of identified peptide; and
normalizing intensities of glycation free b-ions and glycation free y-ions; and (6) selecting novel glycation peptides and advanced glycation end-product peptides showing a similar pattern to the regular pattern generated in step (5) but having a molecular weight difference due to having one or more glycation transformations.

10. The method for identifying glycation proteins and advanced glycation end-products according to claim 9, wherein step (6) is performed by calculation with Mathematical Formula 1:

$$RPS = \frac{\sum_{i=1}^{n} S_i \times S'_i}{\sqrt{\sum_{i=1}^{n} S_i^2 \times \sum_{i=1}^{n} S'^2_i}}$$ [Mathematical Formula 1]

wherein:
S: mass (x) and relative peak intensity (y) of tandem mass spectrometry spectrum,
Si: (x, y) is a vector of peptide mass spectrum patterns, wherein x is the $n^{th}$ relative peak intensity, and y is the $n^{th}$ peak mass, and
S'i: (x', y') is a vector of peptide mass spectrum patterns, wherein x' is the $n^{th}$ relative peak intensity, and y' is the $n^{th}$ peak mass).

11. The method for identifying glycation proteins and advanced glycation end-products according to claim 9, wherein step (6) further comprises evaluating the selected glycation peptides and advanced glycation end-product peptides using molecular weight difference (shift).

12. The method for identifying glycation proteins and advanced glycation end-products according to claim 9, wherein step (6) further comprises analyzing the selected glycation peptides and advanced glycation end-product peptides quantitatively.

13. The method for identifying glycation proteins and advanced glycation end-products according to claim 12, wherein the analyzing step is performed by combining the intensities of the three theoretically strongest peaks among the isotope peaks presenting the intensities of the glycation peptides and advanced glycation end-product peptides selected from MS spectra.

14. A method for identifying glycation proteins and advanced glycation end-products comprising the following steps:

(1) obtaining mass spectrum by analyzing polypeptides obtained from hydrolysis of protein included in a sample with a high-resolution mass spectrometer;

(2) converting the mass spectrum obtained in step (1) into MS (mass spectrum) and tandem spectrum (MS/MS);

(3) identifying peptides from the tandem spectrum converted in step (2);

(4) grouping the peptides identified in step (3) according to peptide sequence into:
group (a): non-glycation peptides; and
group (b): glycation peptides and advanced glycation end-products having one or more glycation transformation(s) occurring at lysine amino acid residue(s) and/or arginine amino acid residue(s) other than C-terminal lysine amino acid residue(s) and/or arginine amino acid residue(s);

(5) generating a regular pattern by:
extracting a mass value and an intensity of glycation free b-ions or glycation free y-ions in tandem spectrum of identified peptide; and
normalizing intensities of glycation free b-ions and glycation free y-ions; and (6) selecting novel glycation peptides and advanced glycation end-product peptides showing a similar pattern to the regular pattern generated in step (5) but having one or more glycation transformations selected from the group consisting of fructosylation (FL), carboxyethyl (CEL), carboxymethyl (CML) and/or methylglyoxal-derived hydroimidazolene (MG-H11).

15. The method for identifying glycation proteins and advanced glycation end-products according to claim 14, wherein the selected novel glycation peptides and advanced glycation end-product peptides show a similar pattern to the regular pattern generated in step (5) but having a molecular weight difference due to having the one or more glycation transformations.

16. The method for identifying glycation proteins and advanced glycation end-products according to claim 14, wherein step (6) is performed by calculation with Mathematical Formula 1:

$$RPS = \frac{\sum_{i=1}^{n} S_i \times S'_i}{\sqrt{\sum_{i=1}^{n} S_i^2 \times \sum_{i=1}^{n} S'^2_i}}$$ [Mathematical Formula 1]

wherein:
S: mass (x) and relative peak intensity (y) of tandem mass spectrometry spectrum,
Si: (x, y) is a vector of peptide mass spectrum patterns, wherein x is the $n^{th}$ relative peak intensity, and y is the $n^{th}$ peak mass, and
S'i: (x', y') is a vector of peptide mass spectrum patterns, wherein x' is the $n^{th}$ relative peak intensity, and y' is the $n^{th}$ peak mass), and
(ii) analyzing the selected glycation peptides and advanced glycation end-product peptides quantitatively, wherein the analyzing is performed by combining the intensities of the three theoretically strongest peaks among isotope peaks presenting the intensities of the glycation peptides and advanced glycation end-product peptides selected from MS spectra.

17. The method for identifying glycation proteins and advanced glycation end-products according to claim 14, wherein step (6) further comprises evaluating the selected glycation peptides and advanced glycation end-product peptides using molecular weight difference (shift).

* * * * *

SEQUENCE LISTING

<160> NUMBER OF SEQ ID NOS: 1

<210> SEQ ID NO 1
<211> LENGTH: 17
<212> TYPE: PRT
<213> ORGANISM: Artificial

-continued

```
<220> FEATURE:
<223> OTHER INFORMATION: isolated polypeptide for identifying
      glycosylation sites_

<400> SEQUENCE: 1

Ser Leu His Thr Leu Phe Gly Asp Lys Leu Cys Thr Val Ala Thr Leu
1               5                   10                  15

Arg
```